(12) United States Patent
Woll

(10) Patent No.: US 7,819,874 B2
(45) Date of Patent: Oct. 26, 2010

(54) CLAVICLE REPAIR DEVICE AND ORTHOPEDIC INTRAMEDULLARY FIXATION SYSTEM

(75) Inventor: Christian Woll, Littleton, MA (US)

(73) Assignee: Woll Bioorthopedics LLC, Littleton, MA (US)

( * ) Notice: Subject to any disclaimer, the term of this patent is extended or adjusted under 35 U.S.C. 154(b) by 1345 days.

(21) Appl. No.: 10/631,529

(22) Filed: Jul. 31, 2003

(65) Prior Publication Data

US 2005/0027294 A1 Feb. 3, 2005

(51) Int. Cl.
*A61B 17/56* (2006.01)

(52) U.S. Cl. .......................................... 606/62; 606/64

(58) Field of Classification Search ................. 606/62, 606/63, 64, 72, 73, 95, 300–301, 303–313, 606/319, 67
See application file for complete search history.

(56) References Cited

U.S. PATENT DOCUMENTS

| | | | | |
|---|---|---|---|---|
| 3,779,239 A | * | 12/1973 | Fischer et al. .................. 606/63 |
| 4,091,806 A | * | 5/1978 | Aginsky ....................... 606/63 |
| 4,237,875 A | * | 12/1980 | Termanini ..................... 606/63 |
| 4,453,539 A | * | 6/1984 | Raftopoulos et al. .......... 606/63 |
| 4,530,355 A | * | 7/1985 | Griggs ........................ 606/105 |
| 5,112,333 A | * | 5/1992 | Fixel ........................... 606/62 |
| 5,397,328 A | * | 3/1995 | Behrens et al. ................ 606/63 |
| 6,048,343 A | * | 4/2000 | Mathis et al. ................. 606/72 |
| 6,090,111 A | * | 7/2000 | Nichols ........................ 606/61 |
| 6,740,086 B2 | * | 5/2004 | Richelsoph ................... 606/60 |

* cited by examiner

*Primary Examiner*—Thomas C Barrett
*Assistant Examiner*—Christine L Nelson
(74) *Attorney, Agent, or Firm*—Cotman IP Law Group, PLC

(57) ABSTRACT

A bone segment positioning device including a base shaft, wherein the base shaft includes a base mating structure and an anchoring thread for securing the base shaft to a distal portion of a broken bone. Additionally, a collar shaft is provided, wherein the collar shaft includes a stabilizer base and a collar mating structure configured for associating with the base mating structure to secure the base shaft to the collar shaft. Moreover, a stabilizing device is provided, wherein the stabilizing device includes a collar configured for associating with the stabilizing base to secure the collar shaft with a proximal portion of the broken bone.

5 Claims, 9 Drawing Sheets

CLAVICLE REPAIR DEVICE AND ORTHOPEDIC INTRAMEDULLARY FIXATION SYSTEM

FIELD OF THE INVENTION

This invention relates generally to a support apparatus and more particularly to an intramedullary (IM) support apparatus for supporting broken bones wherein the IM support apparatus is constructed from a malleable material to be controllably configurable.

BACKGROUND OF THE INVENTION

Devices for stabilizing clavicle bones that have been fractured are well known in the art and stabilize the broken bone by providing an axial load force which keeps the fractured ends of the bone in contact with each other. Referring to FIG. 1, these IM fixation devices typically include anchoring threads disposed on an anterior portion of the IM fixation device and a bone re-association system disposed on a posterior portion of the IM fixation device, wherein the bone re-association system includes a threaded portion and a stabilizing nut. Axial re-association of the fractured portions of the bone is achieved by threading the IM fixation device through both portions of the fractured clavicle bone such that the anterior portion of the IM device is disposed within the IM region of the anterior portion of the fractured clavicle bone. The anchoring threads disposed on the anterior portion of the IM device engage the IM region of the anterior portion of the fractured clavicle bone to snugly contain the IM fixation device within the bone.

The posterior portion of known IM fixation devices are often movably disposed within the IM region of the posterior portion of a fractured clavicle bone such that the bone re-association system is protruding from the posterior lateral end of the clavicle bone. The stabilizing nut is rotated to engage the threaded portion of the IM fixation device, thus causing the stabilizing nut to partially traverse the threaded portion of the IM fixation device. As the stabilizing nut traverses the threaded portion, the stabilizing nut pushes the posterior portion of the fractured clavicle bone toward the anterior portion of the fractured clavicle bone. The stabilizing nut is rotated until the anterior and posterior portions of the fractured clavicle bone contact each other, such that the fractured ends of the clavicle bone remain in contact with each other to allow for the accelerated healing of the clavicle fracture.

Unfortunately, existing IM fixation devices have a number of disadvantages associated with them that adversely affect the healing and comfort of the patient. The profile of the bone re-association system prominently protrudes from the posterior lateral end of the clavicle bone. The patient will experience extreme discomfort as even the smallest movement causes pain in the fascia tissue. Further, current IM fixation device designs do not provide torsional resistance to bone fragments. In situations where torsional support can not be provided by bone fragment interstices, current IM fixation device designs allow the fracture surfaces to grind or rub together, compromising the healing process and causing pain.

SUMMARY OF THE INVENTION

The present invention provides an IM fixation device that can reduce the axial, lateral and torsional movement of bone fragments such that the individual bone fragments may be stabilized relative to one another and that has a low profile protrusion to reduce pain in the fascia tissue caused by movement. The IM fixation device according to the invention comprises a bone segment positioning device including a base shaft which has a base mating structure and an anchoring thread securing the base shaft to a distal portion of a broken bone. Additionally, a collar shaft is provided which includes a stabilizer base and a collar mating structure configured for associating with the base mating structure to secure the base shaft to the collar shaft. A stabilizing device is provided which includes a collar configured for associating with the stabilizing base to secure the collar shaft with a proximal portion of the broken bone.

A method is also disclosed for implementing a bone segment positioning device according to the invention. The method includes stabilizing a proximal portion and a distal portion of the fractured bone to axially align the proximal portion with the distal portion. The method further includes accessing the proximal portion of the fractured bone and drilling a proximal access hole in the proximal portion of the fractured bone. Additionally, the method includes threading a base shaft of the bone segment positioning device into an IM cavity of the proximal portion and the distal portion of the fractured bone through the proximal access hole and securing the base shaft to the distal portion of the fractured bone. Moreover, the method includes threading a collar shaft of the bone segment positioning device into the IM cavity of the proximal portion of the fractured bone through the proximal access hole, wherein a portion of the collar shaft protrudes from the proximal access hole. The method further includes mating the base shaft with the collar shaft to form a single support shaft and securing the single support shaft to the proximal portion of the fractured bone by associating a stabilizing device of the bone segment positioning device with the portion of the collar shaft protruding from the proximal access hole, wherein the stabilizing device provides a compression force in the axial direction of the fractured bone to compress the proximal portion and the distal portion of the fractured bone together.

Advantages of the invention include provision of a bone segment positioning device and methodology that involves a safer, minimally invasive surgical procedure which allows for substantially less pain and discomfort for a patient. Further advantages of the invention include the ability to repair fractured bones without the need for "cutdown" at the fracture site, thus greatly reducing or eliminating any nerve and blood vessel disturbance and risk of infection. An additional advantage of the invention is that the bone segment positioning device is easily removable and malleable. The malleability of the device adds an extra degree of safety because the device will bend before breaking.

BRIEF DESCRIPTION OF DRAWINGS

The foregoing and other features and advantages of the present invention will be better understood from the following detailed description of illustrative embodiments, taken in conjunction with the accompanying drawings in which.

DETAILED DESCRIPTION OF THE INVENTION

Figure 1:
FIG. 1 is a side view of an IM fixation device, in accordance with the prior art.
Figure 2:
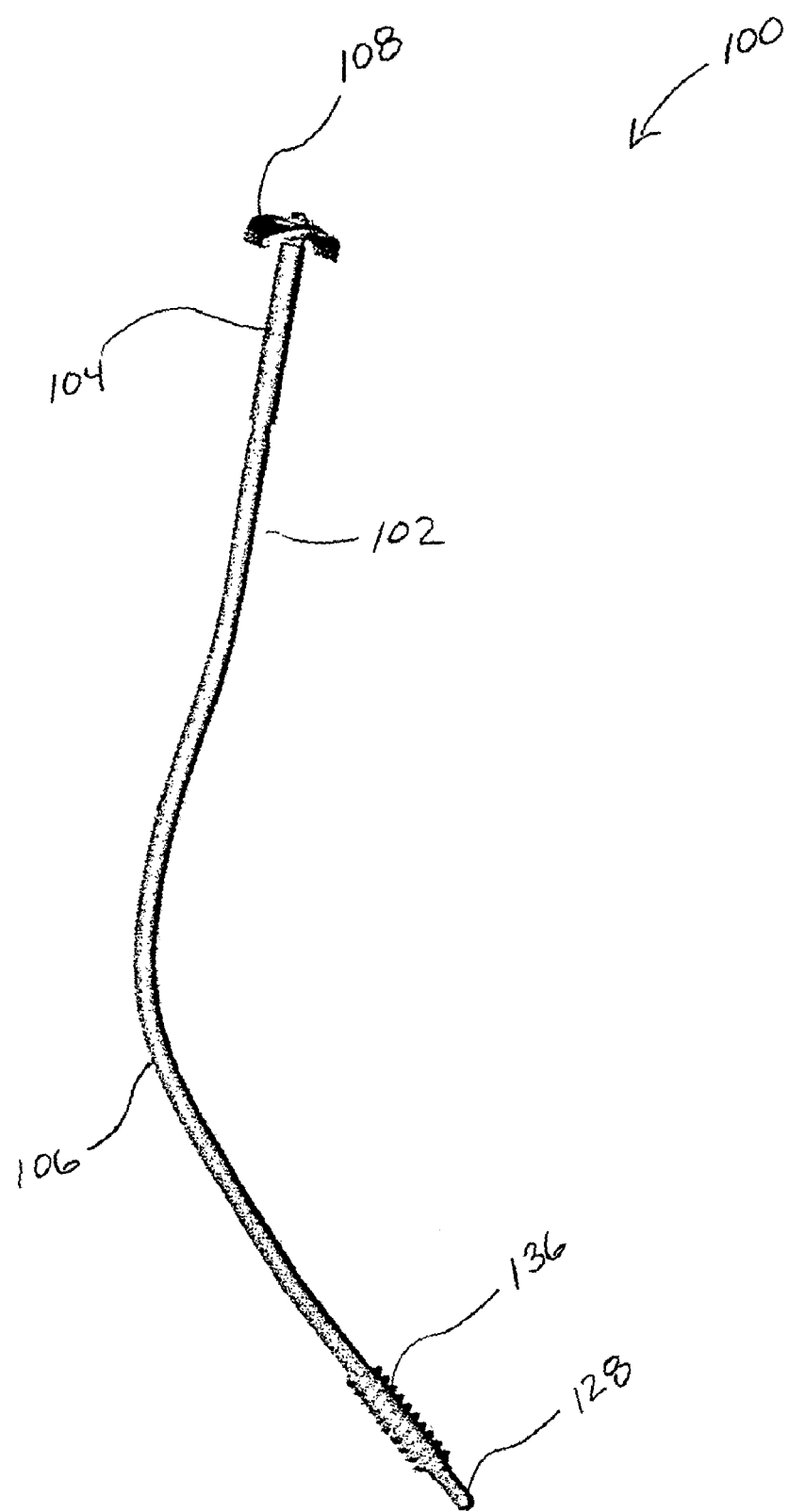
FIG. 2 is a side view of a bone segment positioning device, according to the invention.
Figure 3:
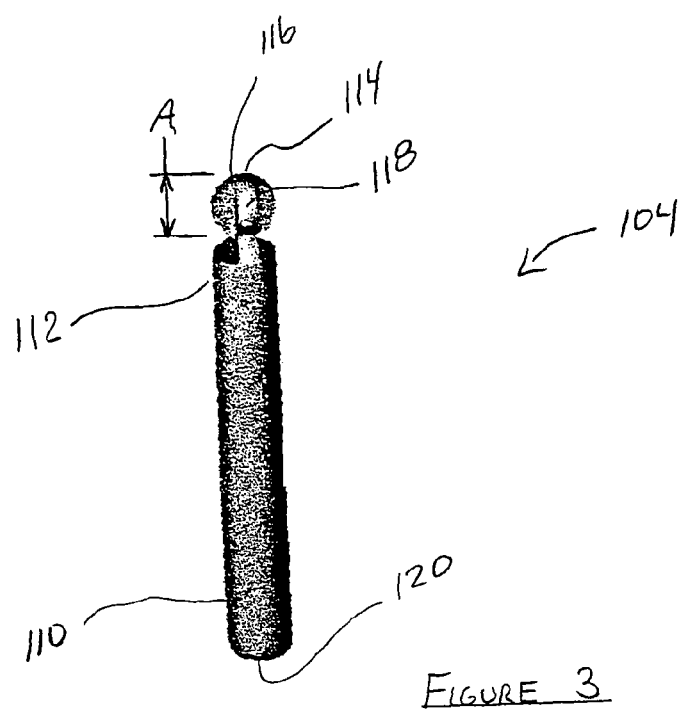
FIG. 3 is side view of a collar shaft of a bone segment positioning device.
Figure 4:
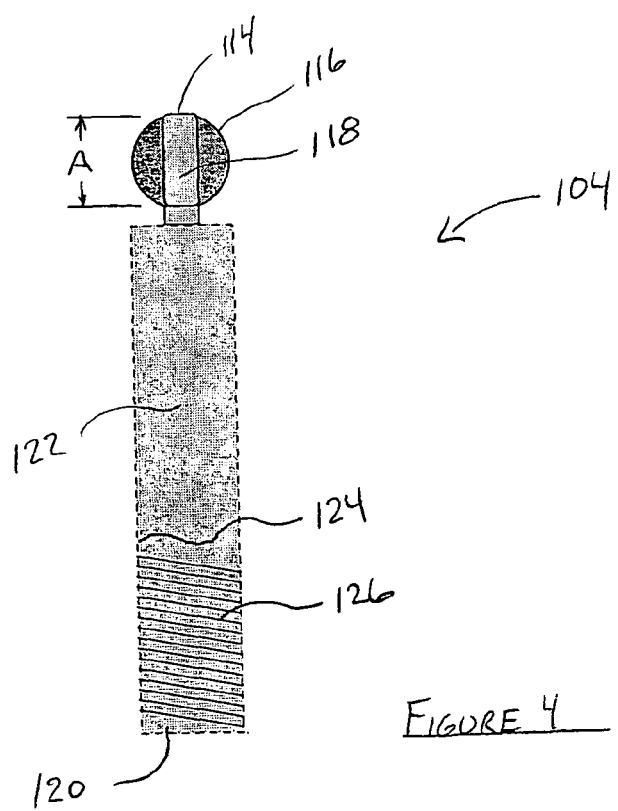
FIG. 4 is a cross-sectional side view of a collar shaft.

Referring to FIG. 2, an illustrative embodiment of a bone segment positioning device 100 is shown and includes a support shaft 102 having a collar shaft 104, a base shaft 106 and a stabilizing device 108. Referring to FIG. 3 and FIG. 4, collar shaft 104 is hollow and constructed from a malleable material and includes a collar shaft distal end 110, a collar shaft proximal end 112 and a stabilizer base 114. The stabilizer base 114 is disposed on collar shaft proximal end 112 and includes a spherically shaped outer surface 116 having a base diameter A and a plurality of key protrusions 118. Collar shaft distal end 110 includes a collar mating structure 120 which defines a collar shaft cavity 122 having an internal cavity wall 124 which includes a threaded portion 126. As disclosed herein, the term 'distal' refers to the element or portion furthest from a patients shoulder and the term 'proximal' refers to the element or portion closest to a patients shoulder.

Figure 5:
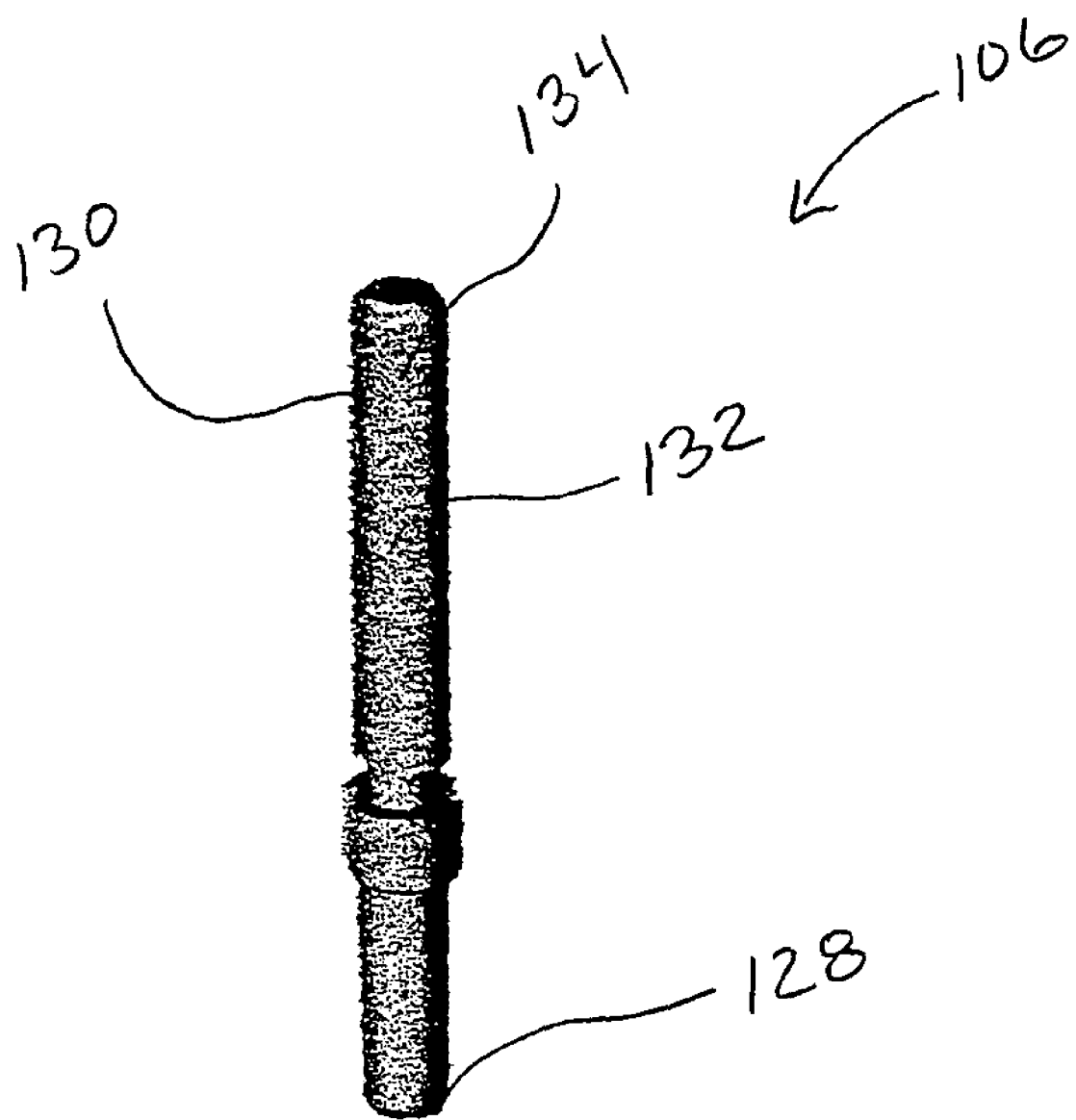
FIG. 5 is a side view of a partial base shaft.

Referring to FIG. 2 and FIG. 5, base shaft 106 is hollow and constructed from a malleable material and includes a base shaft distal end 128 and a base shaft proximal end 130. Base shaft proximal end 130 includes a base mating structure 132 having a base mating thread 134 for engaging threaded portion 126 of internal cavity wall 124. The base shaft distal end 128 includes a self tapping anchoring threads 136 for engaging the IM portion of a bone.

Figure 6:
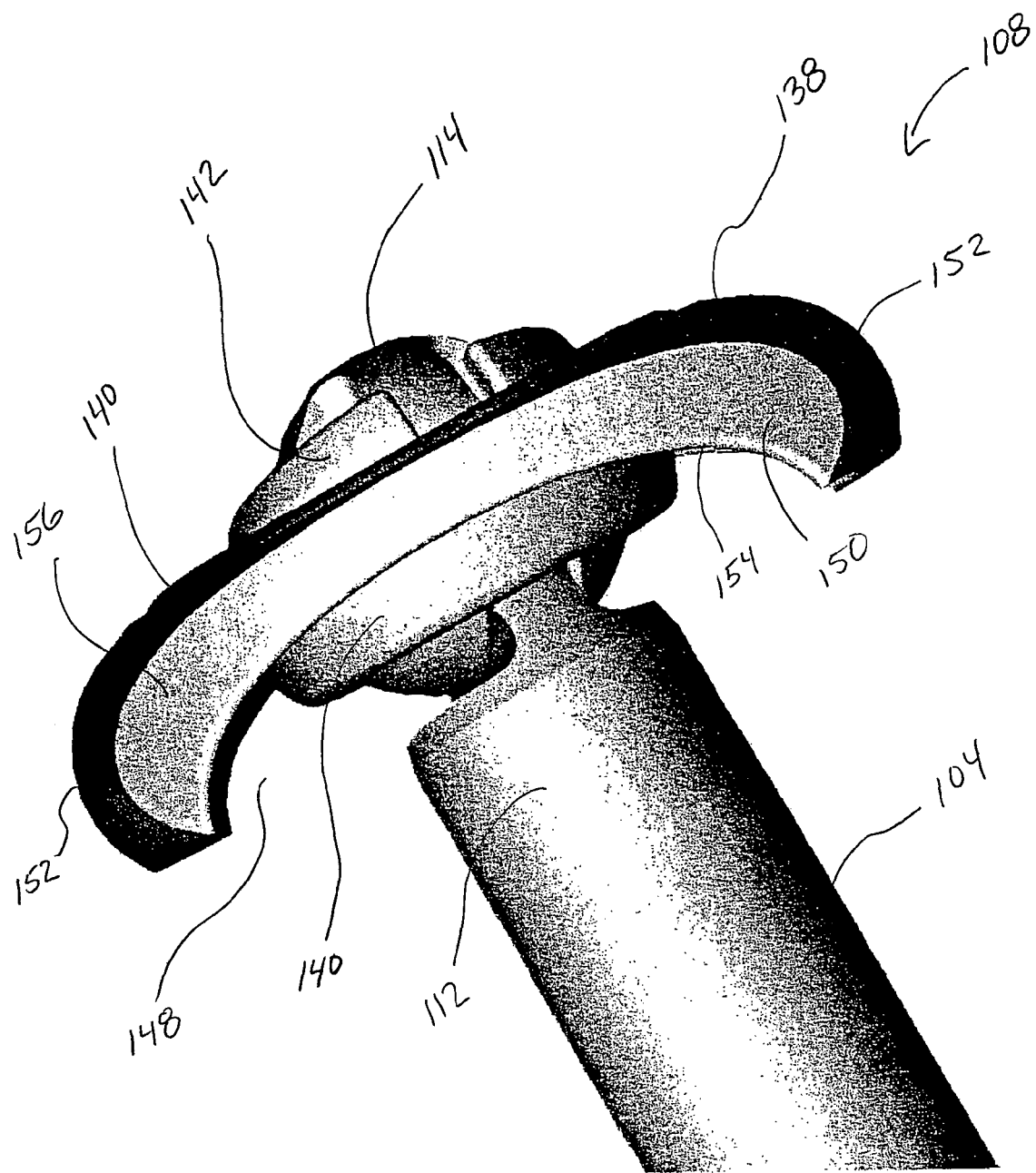
FIG. 6 is a perspective side view of a stabilizing device associated with a collar shaft.
Figure 7:
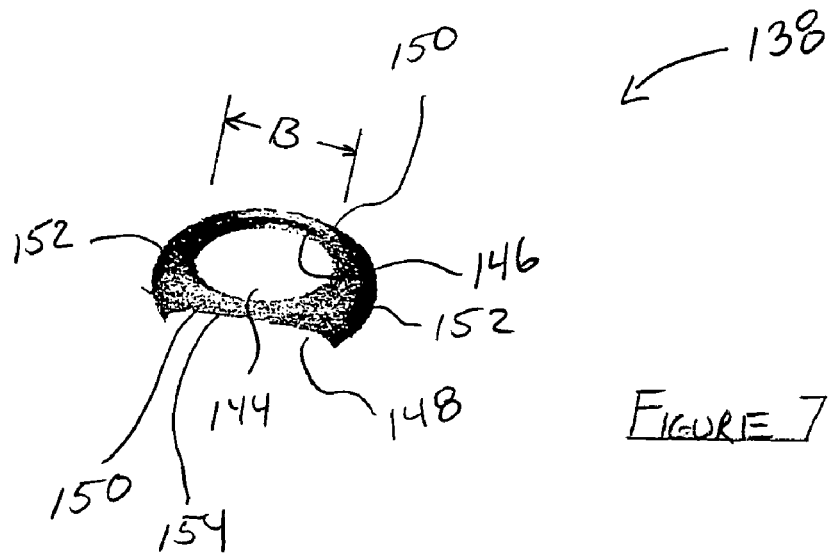
FIG. 7 is a perspective view of a collar.

Referring to FIG. 6, stabilizing device 108 includes a collar 138, a retention sleeve 140 and a fastening sleeve 142. Referring to FIG. 6 and FIG. 7, collar 138 defines a collar cavity 144 having a collar cavity diameter B, wherein collar cavity 144 is circular in shape and includes a beveled cavity edge 146. Collar 138 is substantially oblong in shape to define a collar cradle cavity 148 and includes a plurality of elongated sides 150 and a plurality of shortened sides 152. Each elongated side 150 in this illustrative embodiment includes a crescent shaped notch 154 having a beveled notch edge 156. Each shortened side 152 is rounded to be substantially smooth.

Figure 8:
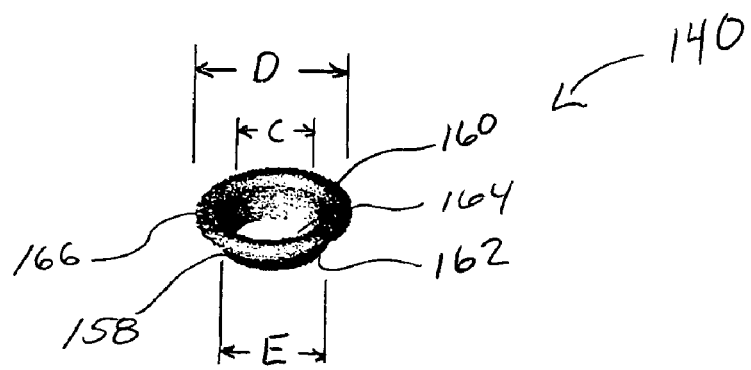
FIG. 8 is a perspective view of a retention sleeve.

Referring to FIG. 8, retention sleeve 140 includes a retention sleeve wall 158 having a retention sleeve wall top 160 and a retention sleeve wall bottom 162. Retention sleeve wall 158 is cylindrical in shape and defines a retention sleeve cavity 164 having a retention sleeve cavity diameter C. Retention sleeve wall 158 includes a sleeve lip 166 originating at retention sleeve wall top 160 and extending away from retention sleeve cavity 164. Moreover, retention sleeve wall top 160 includes a top wall diameter D and retention sleeve wall bottom 162 includes a bottom wall diameter E. Top wall diameter D is larger in size than bottom wall diameter E.

Figure 9:
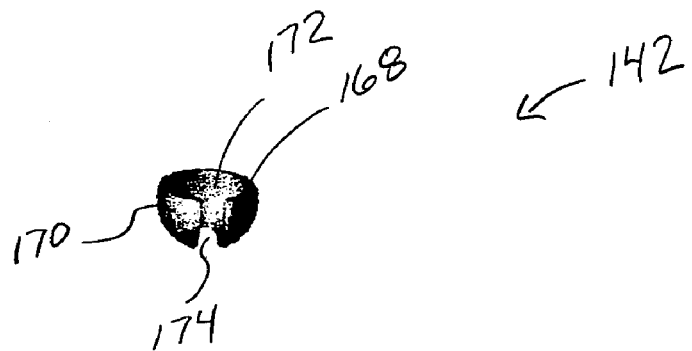
FIG. 9 is a perspective view of a fastening sleeve.
Figure 10:
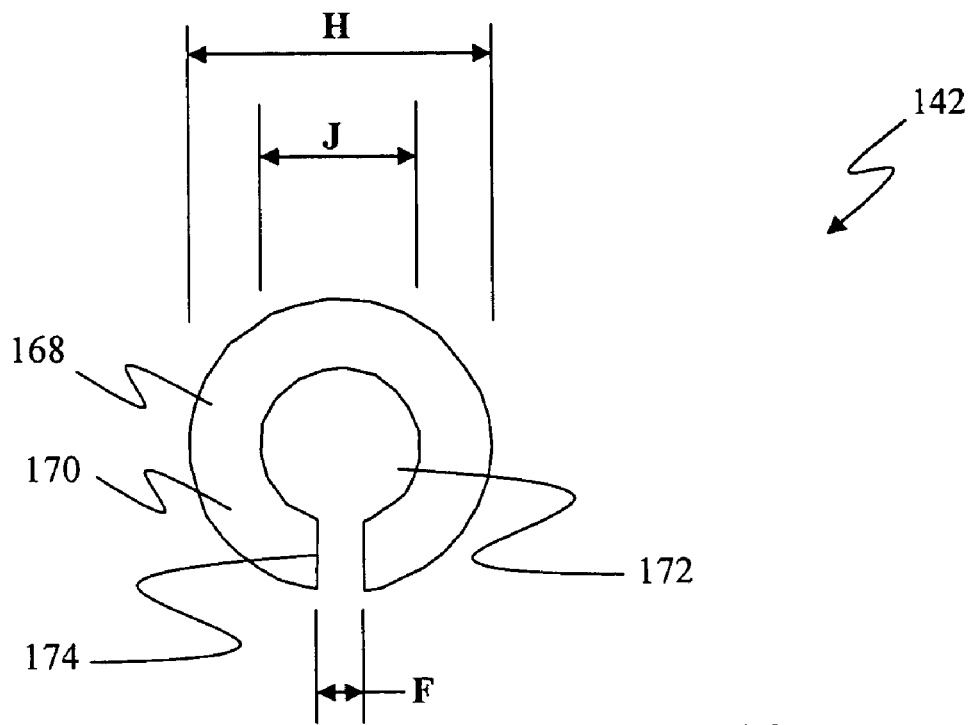
FIG. 10 is a top down view of a fastening sleeve in an expanded configuration.
Figure 11:
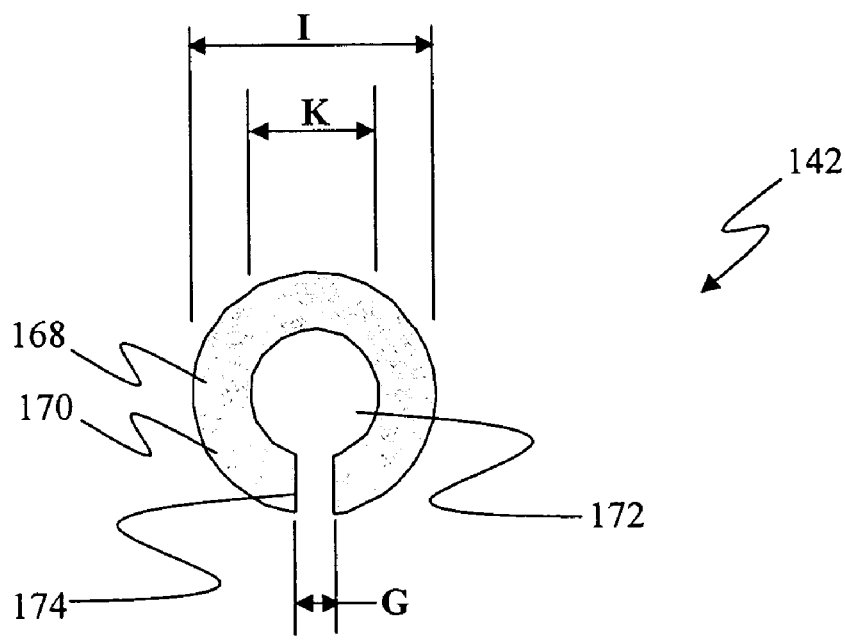
FIG. 11 is a top down view of a fastening sleeve in a compressed configuration.
Figure 12:
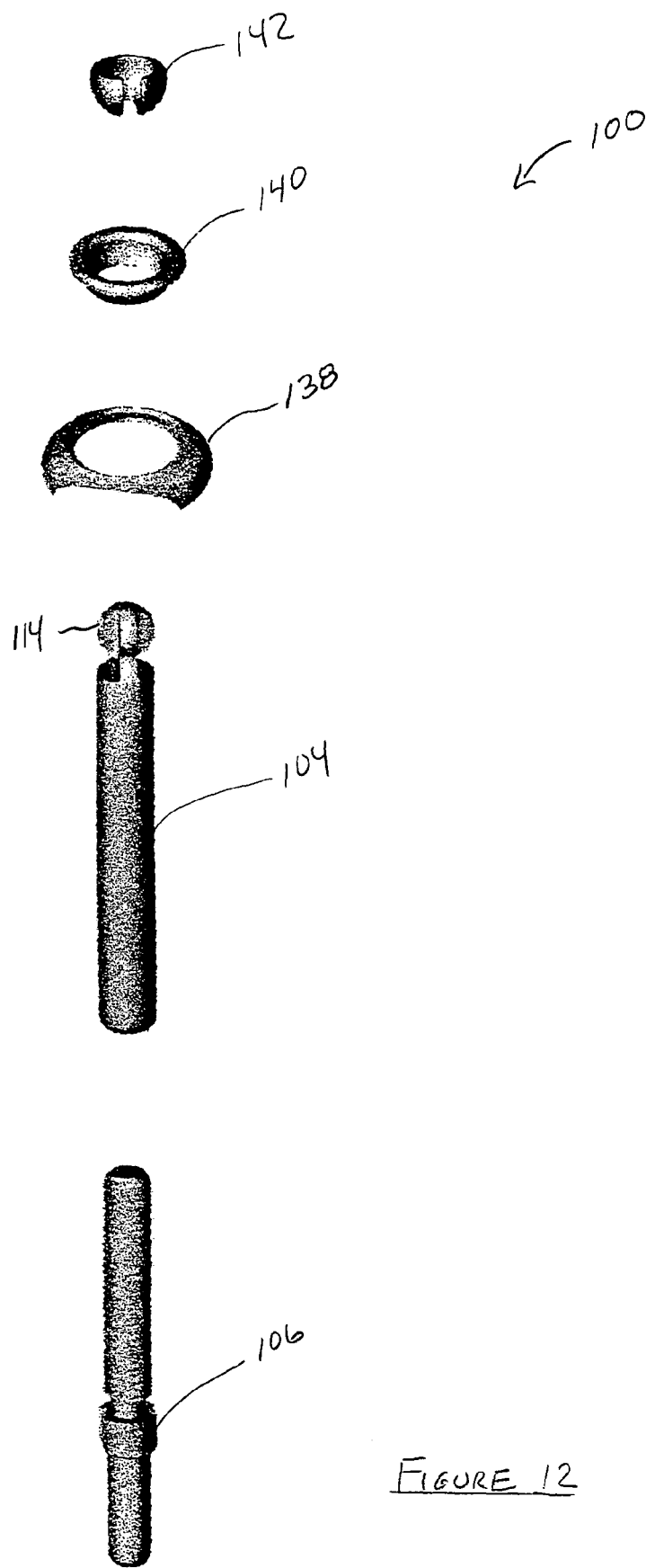
FIG. 12 is an exploded view of a bone segment positioning device.

Referring to FIGS. 9, 10 and 11, fastening sleeve 142 includes a fastening sleeve wall 168 having an arcuate outer surface 170. Fastening sleeve wall 168 defines a cylindrically shaped fastening sleeve cavity 172 and a fastening sleeve notch 174. Fastening sleeve notch 174 includes an expanded notch width F and a compressed notch width G, wherein expanded notch width F is larger than compressed notch width G. Additionally, fastening sleeve wall 168 includes an expanded outer wall diameter H, a compressed outer wall diameter I, an expanded inner wall diameter J and a compressed inner wall diameter K. Expanded outer wall diameter H is larger than compressed outer wall diameter I and expanded inner wall diameter J is larger than compressed inner wall diameter K.

Collar cavity diameter B is sized to be slightly larger than bottom wall diameter E. When retention sleeve 140 is disposed within collar cavity 144, retention sleeve 140 is securely and frictionally contained within. Similarly, retention sleeve cavity diameter C is slightly larger than expanded outer wall diameter H. As such, when fastening sleeve 142 is disposed within retention sleeve cavity 164, retention sleeve wall 158 compresses fastening sleeve wall 168. This compression causes the outer diameter of fastening sleeve wall 168 to be configured from expanded outer wall diameter H to compressed outer wall diameter I. This compression also causes the inner diameter of fastening sleeve wall 168 to be configured from expanded inner wall diameter J to compressed inner wall diameter K and the width of fastening sleeve notch 174 to be configured from expanded notch width F to compressed notch width G.

Referring to FIGS. 6-9 and FIG. 12, retention sleeve 140 is disposed within collar cavity 144. As disposed, sleeve lip 166 is in contact with beveled cavity edge 146. Top wall diameter D is larger than collar cavity diameter B. Therefore, sleeve lip 166 extends over beveled cavity edge 146 and advantageously prevents retention sleeve 140 from traversing completely through collar cavity 144. When retention sleeve 140 is positioned within collar cavity 144, as described hereinabove, stabilizer base 114 is loosely positioned within retention sleeve cavity 164. Fastening sleeve 142 is partially disposed over stabilizer base 114 to align one of the plurality of key protrusions 118 with fastening sleeve notch 174. Fastening sleeve 142 is pressed onto stabilizer base 114. As fastening sleeve 142 is pressed onto stabilizer base 114 fastening sleeve wall 118 is compressed by retention sleeve bottom wall 162. The outer diameter of fastening sleeve wall 168, which has an expanded outer wall diameter H, is compressed by retention sleeve wall bottom 162 to have a compressed outer wall diameter I. Also, as fastening sleeve 142 is pressed onto stabilizer base 114, key protrusion 118 becomes fully positioned with fastening sleeve notch 174. As fastening sleeve wall 118 is compressed by retention sleeve bottom wall 162, the width of fastening sleeve notch 174 is reduced from expanded notch width F to compressed notch width G. This causes key protrusion 118 to be frictionally contained within fastening sleeve notch 174. Moreover, as the outer diameter of fastening sleeve wall 168 is compressed from an expanded outer wall diameter H to a compressed outer wall diameter I, the inner diameter of fastening sleeve wall 168 is reduced from expanded inner wall diameter J to compressed inner wall diameter K, thus compressing stabilizer base 114.

This combination of fastening sleeve notch 174 compressing key protrusion 118 and fastening sleeve wall 168 compressing stabilizer base 114 advantageously allows stabilizer base 114, collar 138, retention sleeve 140 and fastening sleeve 142 to be non-movably and securingly associated with each other. This combination also provides a bone segment positioning device 100 with a low profile design that does not prominently protrude from the clavicle bone. This advantageously promotes the healing process and reduces patient discomfort by reducing device interaction with the fascia tissue. Moreover, the gimbaled design of collar 138 allows the proximal lateral end of the clavicle bone to be cradled within collar cradle cavity 148 restricting torsional movement. This advantageously reduces the risk of damaging blood vessels and thus the risk of infection. When used with a self guiding drill, the bone segment positioning device according to the invention allows for a minimally invasive surgical procedure, increasing the healing time.

Figure 13:
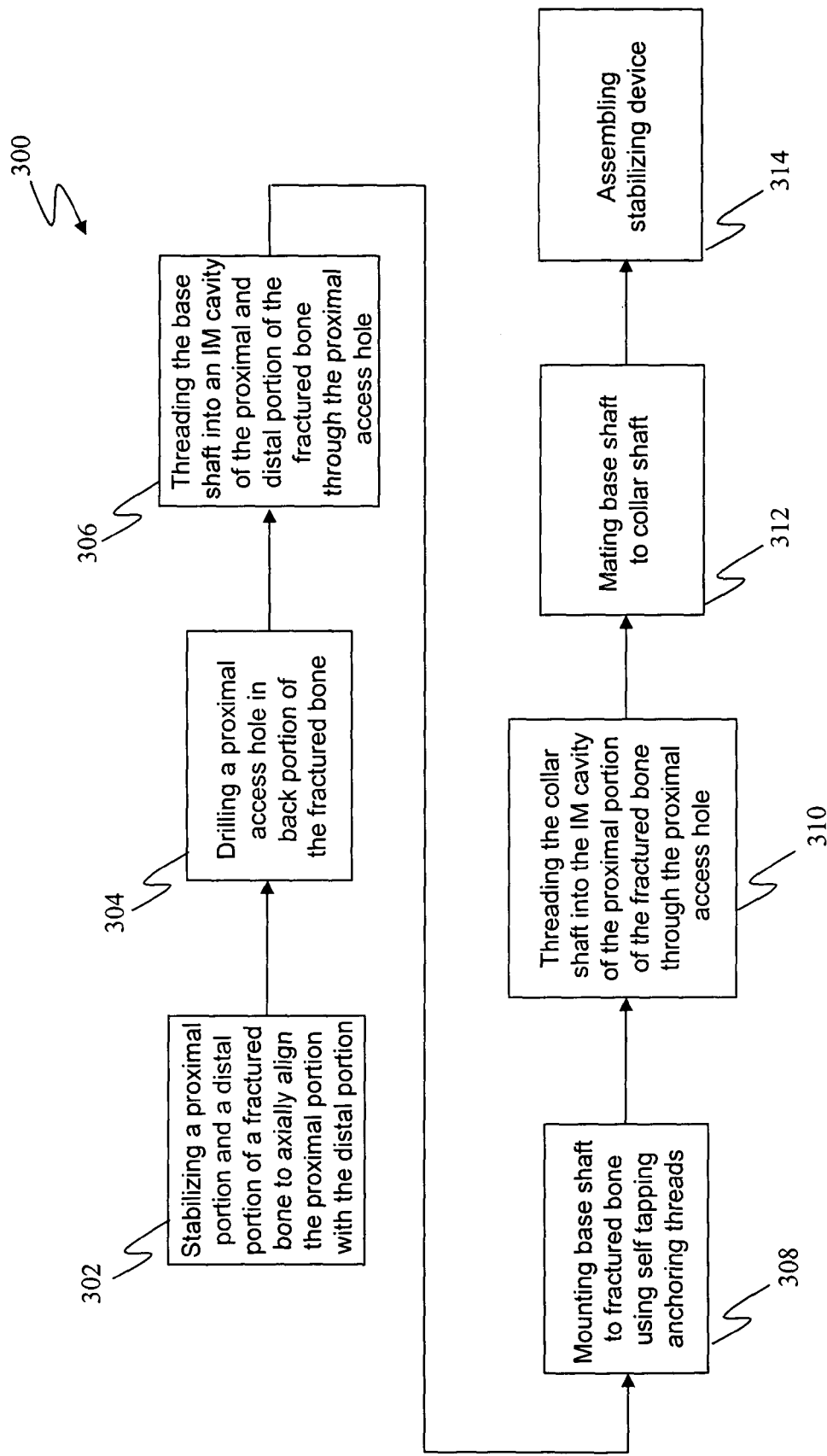
FIG. 13 is a block diagram describing a method for implementing a bone segment positioning device.

Referring to FIG. 13, a method 300 of implementing bone segment positioning device 100 is shown and discussed, in accordance with an exemplary embodiment. When a patient is presented with a fractured clavicle or collar bone, the patient is prepared for surgery and a bone segment positioning device 100 is obtained. The fractured collar bone is stabilized using an external fixation device, or other suitable fixation device as known in the art, to axially align the fractured portions of the collar bone, as shown in block 302. An incision is made in the shoulder area of the patient to allow access to the rear portion of the proximal portion of the fractured clavicle bone. Using a self guiding drill or other suitable drilling device, as known in art, the proximal lateral end of the fractured clavicle bone is then accessed via the incision and a proximal access hole is drilled into the back portion of the fractured clavicle bone at a predetermined angle, as shown in block 304, to allow access to the IM portion of the fractured clavicle bone. The predetermined angle is determined at the time of the surgery and is dependent upon the condition of the fracture. An external and/or an internal fixation device may be used to hold the bone in alignment during the drilling process.

Base shaft 106 is then threaded, base shaft distal end 128 first, through the proximal access hole into the IM cavity of the proximal portion of the fractured clavicle bone and into the IM cavity of the distal portion of the fractured clavicle bone until base shaft distal end 128 contacts the internal surface of the distal portion of the fractured clavicle bone and the base shaft is rotated, as shown in block 306. As the base shaft is rotated pressure is applied to the base shaft to cause self tapping anchoring threads 136 to create an anchoring hole in the distal portion of the fractured clavicle bone. The base shaft is rotated until self tapping anchoring threads 136 are securely associated with the distal portion of the fractured clavicle bone, as shown in block 308. To avoid damaging arteries disposed below the collar bone, care should be taken to ensure that the anchoring hole does not penetrate both sides of the bone by going all the way through the distal portion of the fractured clavicle bone. Base mating structure 132 is protruding from the fractured portion of the distal portion of the fractured clavicle bone.

Collar shaft 104 is then threaded, collar shaft distal end 110 first, through the proximal access hole and into the IM cavity of the proximal portion of the fractured clavicle bone so that collar mating structure 120 protrudes from the fractured portion of the proximal portion of the fractured clavicle bone and stabilizer base 114 protrudes from the proximal anchor hole, as shown in block 310. At this point, collar mating structure 120 and base mating structure 132 are aligned and in contact with each other. Collar shaft 104 is then rotated such that collar mating structure 120 and base mating structure 132 securingly engage each other, as shown in block 312. Stabilizing device 108 is then assembled as disclosed hereinabove so that the proximal and distal portions of the fractured clavicle bone are compressed together and securely held in place, as shown in block 314.

When collar shaft and base shaft are mated together and the stabilizing device is associated with the collar shaft, the bone segment positioning device 100 provides a stabilizing force in the axial direction of the broken bone. This advantageously restricts torsional mobility of the bones and causes the fracture portion of the bone segments to be compressingly held together which promotes rapid healing.

The bone segment positioning device 100 in the illustrative embodiment is fabricated from a biocompatible material or a plurality of biocompatible materials, such as polymerics and/or resorbable materials. For example, the device may be made of poly propylene glycol-co-fumaric acid (PPF), composites and/or metals, such as for example, hafnium, tantalum, titanium, niobium, rhenium or the like and/or alloys, such as nickel-titanium (nitonol) or the like. Additionally, the device may be made of synthetic high polymers, such as for example, polyester; poly-glycollic acid, poly-lactic acid, poly-L-lactic acid, poly-D-lactic acid, poly-D, L-lactic acid, poly-caprolacton, poly-dioxanone, poly-lacton, poly-(.alpha.-malic acid), poly-(.beta.-malic acid), poly-(.alpha., .beta.-malic acid), polyamino acid; poly-glutamic acid, poly-aspartic acid, polycarbonate; poly-trimethylene carbonate, poly-(.alpha.-cyanoacrylate); poly-(.alpha.-cyanoacrylate), anhydride; poly-anhydride, ortho ester; poly-ortho ester having nitrogen-phosphorus bond; poly-phosphazen, and natural high polymers, such as for example, polyester; poly-hydroxybutyric acid, poly-hydroxyvaleric acid, polypeptide; gelatin, collagen, polyphosphate, polyglycoside; starch and chitin or the like.

The biocompatible materials are rigid to provide axial bone re-association strength and malleable to allow the shape of bone segment positioning device 100 to be configurable. This advantageously allows the shape of bone segment positioning device 100 to be configured to conform to the shape of the clavicle bone. It should be appreciated by one skilled in the art that other materials and/or fabrication methods suitable for assembly and manufacture, in accordance with the present disclosure, also would be appropriate.

It should be understood that bone segment positioning devices have very broad utility across a wide spectrum of orthopedic bone repair applications and while the bone segment positioning device as disclosed herein is discussed with regard to the repair of a fractured clavicle bone, it is contemplated that the bone segment positioning device may be used for repair and/or support of other bones and platform technologies as well. It should be understood the in the context of this disclosure the terms broken and fractured used in conjunction with a bone includes greenstick fractures, displace fractures, plastic deformity, torus (buckle) fractures, growth plate fractures, closed fractures, open (compound) fractures, comminuted fractures, pathological fractures and stress fractures.

While the invention has been described with reference to an exemplary embodiment, it should be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims.

What is claimed is:

1. An intermedullary apparatus for providing compressive fixation of a bone comprising:
   a base shaft having a base shaft proximal end and a base shaft distal end comprising an anchoring thread configured to secure said base shaft distal end to a distal portion of a broken bone from within an intermedullary canal of said broken bone;

a collar shaft having a collar shaft proximal end comprising a stabilizer base with a spherical outer surface and a collar shaft distal end configured to couple with said base shaft proximal end;

a collar configured to rotationally couple with said spherical outer surface of said stabilizer base, said collar comprising a cradle cavity configured to couple with an exterior surface of said broken bone; and at least one sleeve positioned between said collar and said stabilizer base, said at least one sleeve configured to compressively couple said collar with said stabilizer base.

2. The intermedullary apparatus of claim 1 wherein said at least one sleeve comprises a circular retention sleeve positioned in said cradle cavity and a circular fastening sleeve positioned between said retention sleeve and said stabilizer base, wherein said retention sleeve comprises a sleeve lip configured to retain said collar, and wherein said fastening sleeve comprises a notch configured to couple with at least one key protrusion of said stabilizing base.

3. The intermedullary apparatus of claim 2, wherein said fastening sleeve comprises an inner wall diameter, an outer wall diameter and a notch width, wherein said inner wall diameter, said outer wall diameter and said notch width are reduced when said fastening sleeve is compressed.

4. The device of claim 1, wherein said collar is substantially oblong in shape, and wherein said collar includes a plurality of elongated sides and a plurality of shortened sides.

5. The device of claim 4, wherein each elongated side includes a crescent shaped notch having a beveled notch edge, and each of said shortened sides is smoothly rounded.

* * * * *